(12) United States Patent
Palatnik

(10) Patent No.: US 8,083,684 B2
(45) Date of Patent: Dec. 27, 2011

(54) INTUBATION VERIFICATION AND RESPIRATORY GAS MONITORING DEVICE AND THE METHOD THEREOF

(76) Inventor: Eugene Palatnik, Pewaukee, WI (US)

( * ) Notice: Subject to any disclaimer, the term of this patent is extended or adjusted under 35 U.S.C. 154(b) by 1261 days.

(21) Appl. No.: 11/748,465

(22) Filed: May 14, 2007

(65) Prior Publication Data

US 2007/0261698 A1 Nov. 15, 2007

Related U.S. Application Data

(60) Provisional application No. 60/800,465, filed on May 15, 2006.

(51) Int. Cl.
*A61B 5/08* (2006.01)
(52) U.S. Cl. ............... 600/532; 600/529; 73/23.3
(58) Field of Classification Search ............ 600/529, 600/532, 538; 128/207.14, 204.22, 204.23; 606/108, 185–230; 73/23.3; 422/84
See application file for complete search history.

(56) References Cited

U.S. PATENT DOCUMENTS

| | | | |
|---|---|---|---|
| 4,879,999 A | 11/1989 | Leiman et al. | |
| 5,166,075 A | 11/1992 | Fehder | |
| 5,179,002 A | 1/1993 | Fehder | |
| 5,445,160 A | 8/1995 | Culver et al. | |
| 5,468,451 A | 11/1995 | Gedeon | |
| 5,517,985 A | 5/1996 | Kirk et al. | |
| 5,679,884 A | 10/1997 | Kirk | |
| 5,957,127 A * | 9/1999 | Yamamori et al. | 128/204.22 |
| 6,190,327 B1 * | 2/2001 | Isaacson et al. | 600/529 |
| 6,502,573 B1 | 1/2003 | Ratner | |
| 6,929,008 B2 | 8/2005 | Geist | |
| 2004/0260194 A1 * | 12/2004 | Bayer et al. | 600/529 |
| 2005/0235995 A1 * | 10/2005 | Tresnak et al. | 128/207.14 |
| 2005/0245836 A1 * | 11/2005 | Star et al. | 600/532 |
| 2006/0009707 A1 * | 1/2006 | Daniels et al. | 600/532 |
| 2008/0200825 A1 * | 8/2008 | Rich et al. | 600/532 |

\* cited by examiner

*Primary Examiner* — Miranda Le
*Assistant Examiner* — Eric Messersmith
(74) *Attorney, Agent, or Firm* — Intellectual Property Law Group LLP; Juneko Jackson

(57) ABSTRACT

A patient vital sign monitoring device and method thereof is described. According to an embodiment of the present invention there is a portable, lightweight, and small device which verifies intubation and monitors respiratory gas in a patient. The device comprises an electronic monitoring device portion and a disposable airway adapter, the disposable airway adapter having an integral display for indicating presence or levels of respiratory gas. A method for respiratory gas monitoring according to an embodiment is provided comprising connecting a disposable airway adapter to a tube in a patient's body, the adapter having an integrally attached display portion for displaying information; releasably attaching an electronic monitoring device portion to said airway adapter; determining proper tube insertion by measuring the respiratory gas of said patient through the monitoring device, as displayed through said display portion; and releasing said monitoring device portion from said airway adapter.

17 Claims, 4 Drawing Sheets

INTUBATION VERIFICATION AND RESPIRATORY GAS MONITORING DEVICE AND THE METHOD THEREOF

CROSS-REFERENCE TO RELATED APPLICATION

This application claims priority to U.S. provisional patent application Ser. No. 60/800,465, filed on May 15, 2006, which is hereby incorporated by reference in its entirety.

BACKGROUND OF INVENTION

1. Field of Invention

Aspects of the present invention relate to a medical device for and method of monitoring the vital signs of a patient. In particular, there is a device for intubation verification and respiratory gas monitoring, and a method thereof.

2. Background

Endotracheal intubation into the trachea of a patient is well-known and widely used in practice. Such intubation is performed when normal ventilation of the patient's lungs may be impaired. Failure to artificially ventilate an apneic patient rapidly could result in serious brain damage or death.

During patient intubation, a flexible tube, also known as an endotracheal tube is used; wherein a distal end of the tube is placed within the patient's trachea. The proximal end of the tube can be attached to a resuscitator bag or any other device, supporting the respiratory process. During patient intubation, there is a risk of an accidental misplacement of the endotracheal tube into the esophagus. This condition can in itself cause death and disability if not quickly detected.

A patient consumes oxygen and exhales carbon dioxide during the respiratory process. Thus, sensing of carbon dioxide in a patient's exhaled gas is commonly used to detect proper placement of endotracheal tube.

In addition, as the endotracheal tube is properly installed into the trachea, it is clinically important to monitor the production of carbon dioxide to maintain adequacy of patient resuscitation. Normally there is 5% of carbon dioxide present in a patient's exhaled esophageal gas, indicating proper placement of an endotracheal tube as well as adequate resuscitation or ventilation.

In the prior art, two major categories of carbon dioxide detectors have been described. One of these categories includes devices which utilize chemical calorimetric carbon dioxide detectors. In many cases, devices are single patient use and disposable. The detector of such devices includes a chemical substance, which changes its color in presence of carbon dioxide. By looking at the change in color, a caregiver can verify presence of carbon dioxide in a patient's exhaled gas. Although calorimetric detectors are portable, light weight disposable devices, and widely utilized in practice, they suffer from significant disadvantages.

One of the many disadvantages is that the color change is not visible in a reduced lighting environment, such as in ambulances, in fire or car accident scenes at night, etc. These devices have a relatively short shelf life, since the chemical substance deteriorates with time; thus, the device must be disposed. To assure a large area of color indication, such devices utilize a relatively large gas to surface contact area, thereby increasing "dead space"—extra volume inside the airway adapter, where the inhaled and exhaled gases mix up. This problem reduces not only productivity of resuscitation, but also slows down the color change process in the detector, making it more difficult for a caregiver to reliably observe changes in color.

Another disadvantage is that chemical substances which are sensitive to carbon dioxide are very often sensitive to moisture; condensed moisture and secretions might negatively affect a calorimetric device performance. Furthermore, when being used in "flight for life" patient transportation or high in the mountains, a calorimetric device is not capable of reflecting an accurate percent of carbon dioxide in exhaled gas, since it can not compensate for reduced ambient pressure.

In another category of existing devices electro-optical sensing is utilized. It is well known that carbon dioxide absorbs infrared light. By determining the amount of absorbed infrared light, the presence and concentration of carbon dioxide can be determined.

In one particular existing device, there is described an elector-optical sensing device consisting of: a disposable single patient airway adaptor for passing respiratory gas through, which is detachable from the reusable monitoring portion; a detector used as a part of the monitoring portion, having a light source for irradiating infrared radiation and an infrared radiation detector for detecting the infrared radiation that has passed through the respiratory gas; a monitor body, having a display surface for indicating the concentration of a respiratory carbon dioxide gas, for measuring the concentration of respiratory carbon dioxide gas by receiving a signal from the detecting portion; where the detecting portion is mounted onto the monitor body forming one unit. The monitoring body contains a power source (batteries) to operate the device.

Although this device overcomes some of the disadvantages of calorimetric devices; it however has its disadvantage—a large weight and size; as a result of integrating the detecting portion, power source, and electronic circuitry inside the monitoring body of the device. Such a device having a large weight and size and attached to the endotracheal tube introduces a number of significant problems, including the ease in which it can accidentally pull out the endotracheal tube from the trachea. Another considerable problem occurs in cases of vibration presented in ambulances during patient transportation. A heavy device in close proximity with a patient's face, is likely to injure the patient's skin or eyes.

In the same electro-optical sensing device there is described a detection portion separated from the monitoring body by an electrical cable. Separating the detection portion from the monitor body, which includes the power source, electronic circuitry and display, reduces the weight applied directly to the endotracheal tube. However, splitting the device into two parts connected with electrical cable causes a major inconvenience to the caregiver, requiring the caregiver to hold the monitor body while resuscitating and transporting the patient.

SUMMARY

Accordingly, there is a need for a portable intubation verification and respiratory gas monitoring device that eliminates the aforementioned disadvantages of both calorimetric devices and electro-optical sensing devices.

There is a need to provide for a minimized and lightweight device which does not interfere with a patient's respiratory support and will avoid injuring a patient's face during transportation.

In one aspect of the present invention, there is an intubation verification and respiratory gas monitoring device that is reduced in size and weight than existing devices and further provides for a display portion that is part of a disposable adapter.

In another aspect of the present invention, there is provided an electronic device, thereby overcoming the problems of calorimetric devices, but is structured to be very lightweight and small. In an embodiment, the display is structured as a combination of the reusable electronic device incorporated with the disposable adapter, thereby providing a large enough display for displaying information but at the same time reducing the weight and size of the overall device. The display is integral to the disposable adapter and therefore disposable as well. The device is self-contained and fully autonomous.

According to an embodiment of the present invention there is device for intubation verification and respiratory gas monitoring comprising: a disposable airway adapter including one or more airway connections, at least one connection having an end leading to a patient's body and another end meeting at a sealed airway chamber, the chamber providing for infrared light to pass through; a monitoring device portion having a top surface and a recessed section, the monitoring device being releasably attachable to the airway adapter around the airway chamber at the recessed section; a display portion integrally connected to said airway adapter, having a top surface and a bottom surface, the bottom surface partly resting upon the top surface of the monitoring device during attachment; wherein the monitoring device portion comprises components for emitting infrared light and taking measurements of infrared light energy absorption, and the display portion displays one or more results of said measurements.

In another embodiment of the present invention there is a method of tube insertion verification and respiratory gas monitoring using a respiratory gas monitoring device comprising: connecting a disposable airway adapter to a tube in a patient's body, the adapter having an air chamber and an integrally attached display portion outside said air chamber for displaying information; releasably attaching an electronic monitoring device portion to said airway adapter, such that a top surface of said monitoring device portion rests beneath a bottom surface of said display portion; determining proper tube insertion by measuring the respiratory gas of said patient through the monitoring device, wherein said monitoring device measures respiratory gas by emitting infrared light through said air chamber, sensing light energy absorption, and providing results of said energy absorption to said display portion; and releasing said monitoring device portion from said airway adapter.

Implementations of the present invention include a method of intubation verification, a method of respiratory gas monitoring, and a combination thereof.

These and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Figure 1:
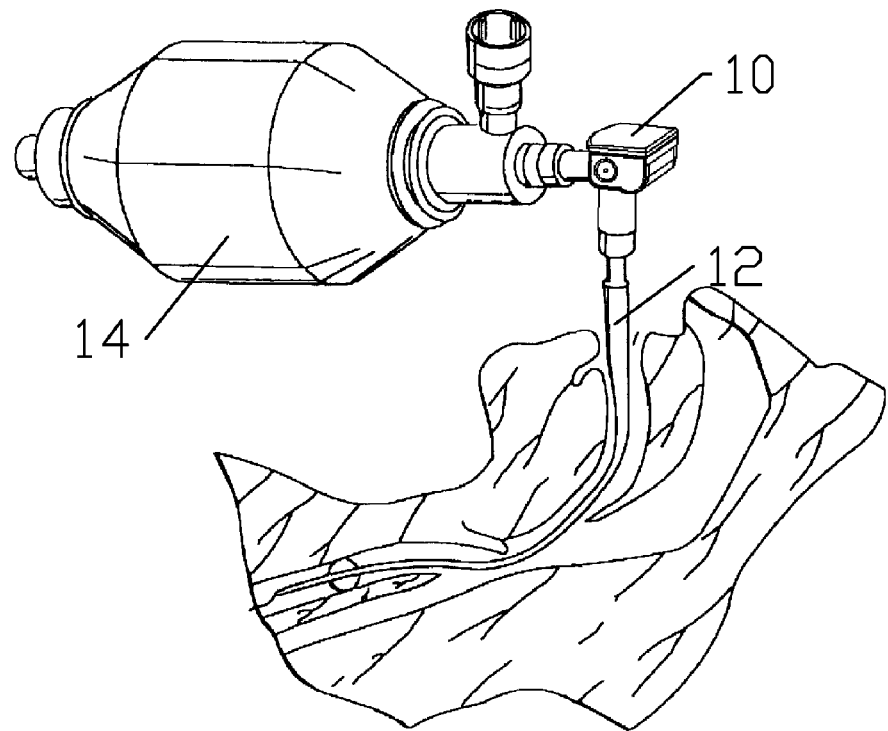
FIG. 1 is a view of an intubation verification and respiratory gas monitoring device installed between endotracheal tube and resuscitator bag, according to an embodiment of the present invention.

According to an embodiment of the present invention, an intubation verification and respiratory gas monitoring device 10 is shown in perspective view installed between endotracheal tube 12 and resuscitator bag 14 as illustrated in FIG. 1.

Figure 2:
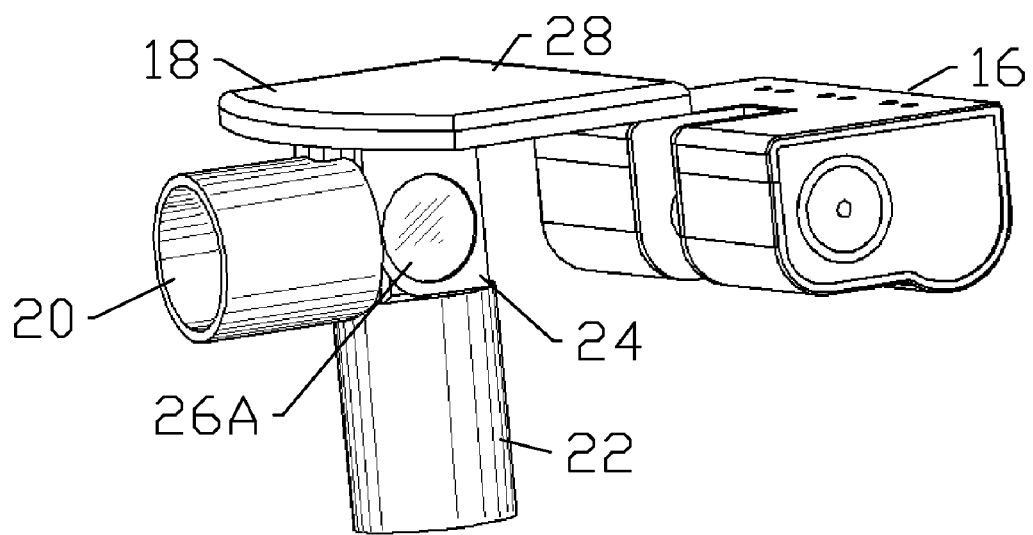
FIG. 2 is a view of the disposable and reusable portions of the device separated, according to an embodiment of the present invention.

Referring now to FIG. 2, intubation verification and respiratory gas monitoring device 10 comprises two parts—disposable airway adapter 18 and reusable monitoring device 16. A caregiver carries monitoring device 16 with him or her, for instance as a keychain or on a lanyard or on any other carrying device. In a preferred embodiment, the monitoring device's case includes a plastic loop to allow attachment to a lanyard or a keychain ring. Disposable airway adapters are supplied in plastic sealed bags to ensure a hygienic environment. Adapter 18 is removed from the sealed bag right before intubation is required; and is disposed together with endotracheal tube as soon as it is removed from a patient's airway to prevent cross-contamination. A simple latching mechanism is used to mate two parts as described hereinafter, according to an embodiment of the present invention.

Disposable airway adapter 18 is made of light clear molded biocompatible plastic material, such as polycarbonate or other similar and suitable material. As shown in FIG. 2, airway adapter 18 includes two standard tubular airway connections 20 and 22, with an external diameter of about 22 mm, and an internal diameter of about 15 mm. Gas passes through tubular connection 22 into the chamber 24. This gas, carbon dioxide, is exhaled by the patient through connection 22 through chamber 24 and evacuated through the flap valve of the resuscitator bag 14. Two windows 26A and 26B, made of thin infrared transparent biocompatible plastic material such as polyethylene or polypropylene are installed on the opposite sides of airway adapter 18. Infrared light passes through the window into the chamber 24, where depending on carbon dioxide concentration; some fraction of light energy is absorbed by the gas. The inner surfaces of the windows are coated with anti-fog coating to minimize fogging due to moisture level changes in the respiration cycle.

Figure 3A:
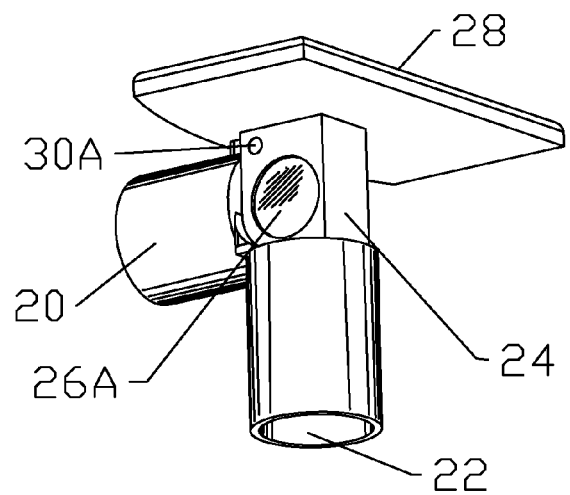
FIG. 3A is a perspective view of the disposable adapter portion from the left side, according to an embodiment of the present invention.
Figure 3B:
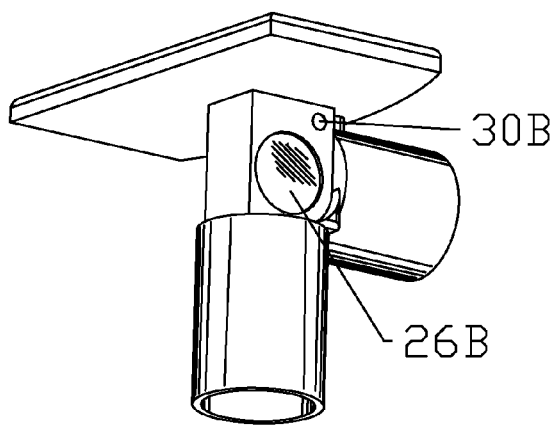
FIG. 3B is a perspective view of the disposable adapter portion of FIG. 3A, from the right side, according to an embodiment of the present invention.

Disposable adapter 18 snap-fits onto monitoring device 16. As shown in FIGS. 2, 3A, and 3B, detents 62A and 62B on the aluminum bracket 42, snap-fit into depressions 30A and 30B on the disposable adapter 18 to securely hold the adapter 18 to the monitoring device 16. In a preferred embodiment, detents 62A and 62B are spring loaded steel balls. As adapter 18 is slid into the monitoring device 16, detents 62A and 62B are pushed against the spring in a channel within the aluminum bracket 42. The detents (steel balls) then spring back out when depressions 30A and 30B are reached and secure the adapter 18 in place with the monitoring device 16. Other connection mechanisms may be similarly implemented. As shown in FIG. 2, FIGS. 3A and 3B, airway adapter 18 also includes a display portion 28, which will be explained hereinafter.

Figure 4:
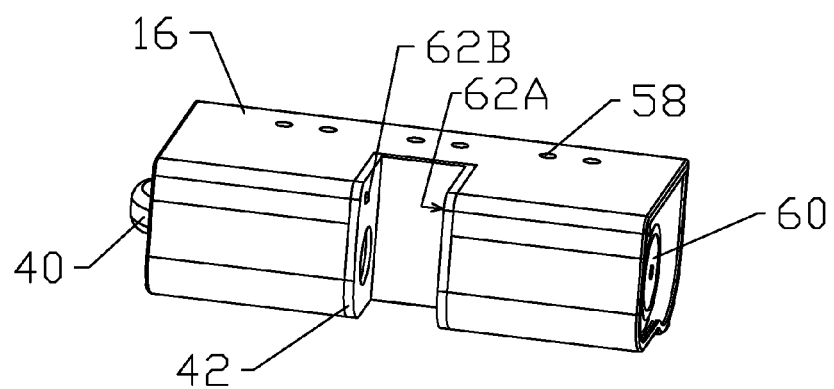
FIG. 4 is a perspective view of the monitoring device portion, according to an embodiment of the present invention.
Figure 5:
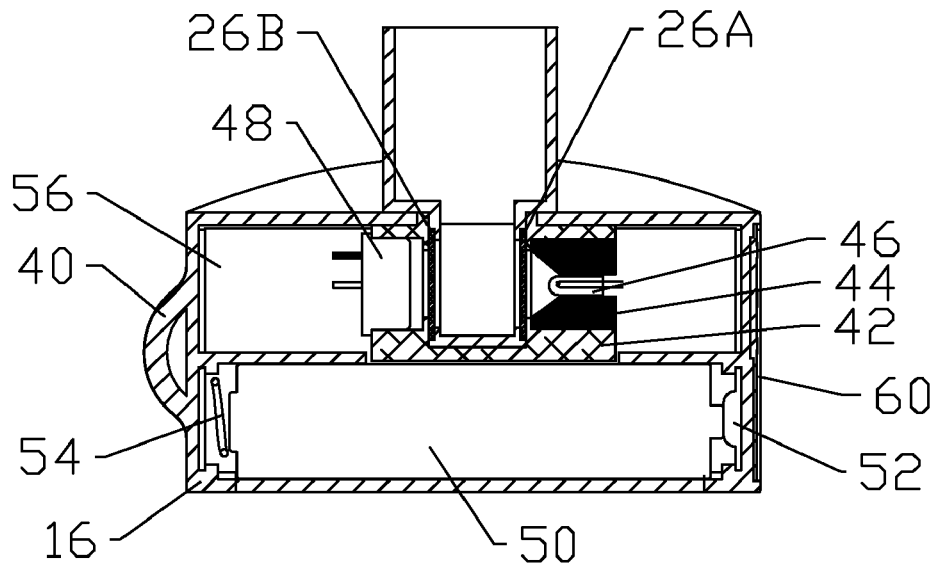
FIG. 5 is a cross-sectional view along a horizontal plane of the device, according to an embodiment of the present invention.
Figure 6:
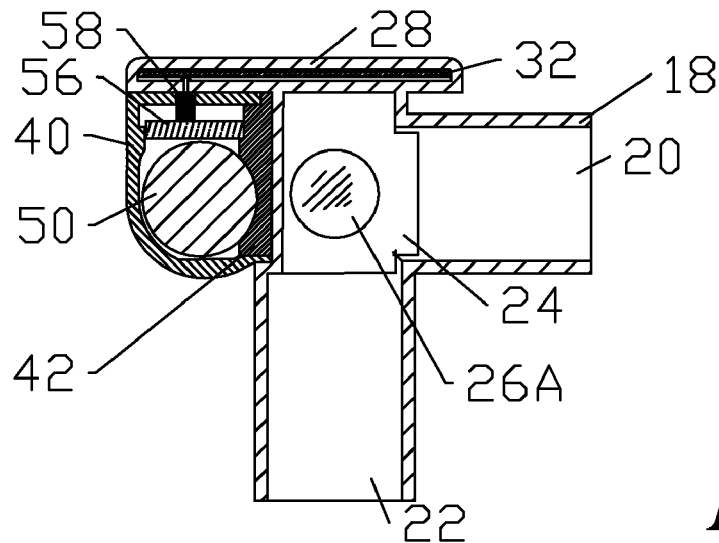
FIG. 6 is a cross-sectional view along a vertical plane of the device, according to an embodiment of the present invention.
Figure 7:
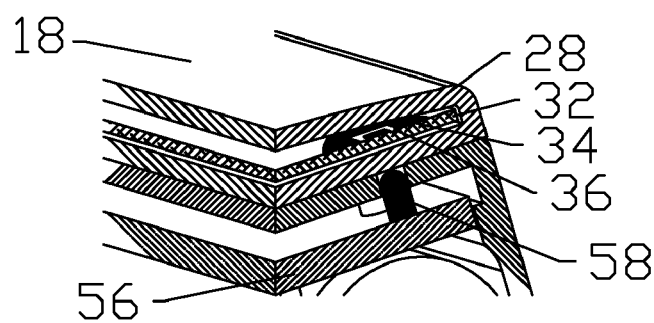
FIG. 7 is an enlarged partial cross-sectional view of the device, along a vertical plane in two directions, according to an embodiment of the present invention.

Monitoring device 16 is further shown in the perspective view of FIG. 4 and in cross-sectional views of FIGS. 5, 6 and 7. It is protectively covered by a plastic case 40, preferably made of ABS plastic. As shown in FIG. 5, a cross-sectional view of the device along a horizontal plane viewed from the bottom, aluminum bracket 42 contains openings for infrared radiator 46 with reflector 44, and infrared sensor 48. Infrared light produced by radiator 46 propagates through window 26A into chamber 24, then through window 26B into sensor 48.

As shown in FIGS. 5 and 6, battery 50 or other power source, resides in its compartment and is connected to a circuit board 56 by means of two battery contacts 52 and 54. Other lightweight power means may be implemented. Circuit board 56 is connected to sensor 48 and to LED's 58. As shown in FIGS. 4 and 5, a membrane On/Off switch 60 turns the device on and off.

FIG. 6 shows a construction of the display portion 28 of airway adapter 18. As mentioned, the major disadvantages of the prior art electro-optical intubation verification and gas monitoring devices are their weight and size. In the device according to an embodiment of the present invention, a display portion is eliminated from the monitoring device altogether. Accordingly, there is no need to include an extended display surface into the monitoring device; which otherwise would add to the size and weight of the enclosure which includes circuit boards, electronic and display components, display screen mechanical and optical parts, etc. Instead, according to an embodiment of the present invention, the display portion 28 is made as an integral part of the disposable adapter 18, by molding of light, clear plastic material as one unit, the display and adapter are made disposable. In a preferred embodiment of the present invention, monitoring device 16 is about 55 mm by 25 mm by 17 mm; and the overall weights of the whole device including AAA battery and disposable adapter 18 is around 28 grams. As such the device is autonomous and self-contained.

As shown on FIG. 6 and FIG. 7, monitoring device 16 includes single discrete LED's 58, installed on the circuit board 56, protruding through the surface of the device. As monitoring device 16 mates with disposable adapter 18, light emitted by LED's 58 travels through the clear bottom surface of the display portion 28 of disposable adapter 18, acting as a light pipe; and then hits the display screen 32. Display screen 32 is made of semi-transparent material such as mylar or waxed paper. Display screen 32 may be sandwiched and sealed inside the display portion 28.

According to this embodiment, display screen 32 is used as a projection screen for very small and directional LED's, located inside monitoring device 16. To further reduce dead space, display screen 32 is hermetically sealed and is separated from chamber 24. As such, there is no excessive dead volume of gas inside adapter 18, otherwise causing a mixture of exhaling and inhaling gases, commonly found in calorimeter devices. Alternatively, the display screen 32 may be placed directly to the top surface of the display portion 28, for instance by adhesive. The display screen may further be covered with a moisture protective surface or sealant. In an embodiment, the display portion comprises a recessed top surface with a higher edge border around the perimeter. The display screen 32 may then be placed on the top surface with an adhesive and therefore be protected around the perimeter.

FIG. 7 further describes construction of a display screen 32. In an embodiment of the device, display screen 32 is silk-screened or pre-printed with opaque paint 34, with exception to the areas 36, which are designated as display images, such as segments of 7-segment indicators, highlighted or colored areas, a respiration bar graph, and other configurations. Display screen 32 may also include printed warning and/or instructional messages.

Graphical display images may vary depending on the device's target use. For example, the display may provide for indicators representing simply "no breath", "low", "good", "high" levels of carbon dioxide concentration. The display may provide for the actual number of carbon dioxide gas concentration. As such, implementation of the device may be incorporated into inter-hospital patient transportation in addition to intubation verification, by indicating the actual value of carbon dioxide required for such transportation.

Figure 8:
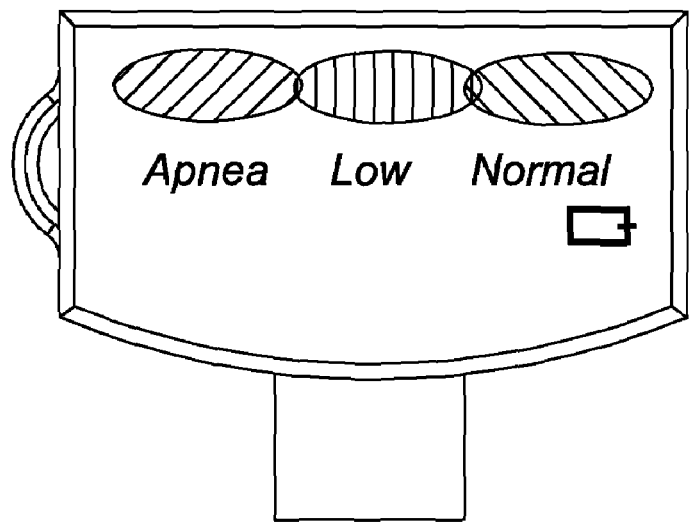
FIG. 8 is a view of the display screen of the device, according to an embodiment of the present invention.

In one embodiment according to the present invention, as shown in FIG. 8, three highlighted areas are utilized. Different color or sensory indicators may be used. For instance, the indicator on the left is red when lit, indicating apnea (or lack of respiration). The central area, being yellow when lit, indicates respiration, but that the exhaled carbon dioxide concentration is low, or below 2% for example. The right side area, being blue when lit, indicates normal respiration with a carbon dioxide level above 2%. As mentioned, the display screen 32 may be sealed within a slot in the display portion 28 or placed on the top surface of the display portion 28. When placed on the top surface of the display portion 28, the display screen 32 may comprise an adhesive, for instance a sticker made of mylar, for attachment, the screen having a non-adhesive semi-transparent portion 36 for instance showing the different colors, and the adhesive portions 34 inhibiting light projection. The screen 32 may be placed onto the display portion 28 by peeling a wax paper off the adhesive portions before placing the screen 32 to the top surface of the display portion 28.

Figure 9:
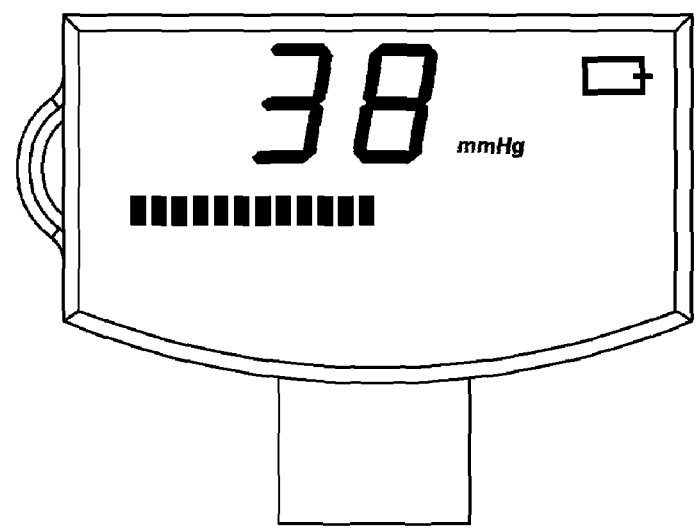
FIG. 9 is a view of the display screen of the device, according to another embodiment of the present invention.

In another embodiment, as shown in FIG. 9, two seven segment indicators are implemented, when lit by LED's. Each segment utilizing a dedicated LED in the monitoring device. In addition, a respiration bar graph is implemented; indicating inhale-exhale cycles.

Various alternatives for the display portion of the device may be contemplated to display an assortment of different information indicators or data from results of the measurements of the energy absorption. Actual results of the measurements, i.e. numbers, percentages, ranges for example, and/or attributes of the measurements, such as yes/no, may be displayed. Different visual indicators, graphics, text, color, or sound or vibration, and any other sensory indicators or combination thereof, may be implemented with the device. In addition, the device may be incorporated to wirelessly connect with a computer network or with another external display device for monitoring the patient.

Other applications of the present invention are considered. In an embodiment of the present invention, there is an implementation for a feeding tube verification device. The method of gas monitoring is incorporated into the device wherein a feeding tube is installed in the patient's esophagus. If carbon dioxide is not detected, then the feeding tube has been installed properly. On the other hand if the display indicates a presence of carbon dioxide, then the feeding tube has been inherently installed improperly because the tube has been placed in the trachea whereby carbon dioxide gas would be detected. As such, the display could indicate the existence or not of gas, thereby verifying the proper placement of the feeding tube. The display portion of the device may indicate a visual "yes" or "no" for the carbon dioxide presence or through some other sensory indication or combination thereof for instance an audio indication. At the same time, the device can be implemented to verify intubation in a patient if needed.

According to another embodiment of the present invention there is a method of tube insertion verification and respiratory gas monitoring using a respiratory gas monitoring device. The method comprises connecting a disposable airway adapter to a tube in a patient's body. The tube may lead to the patient's trachea or esophagus depending on the whether the monitoring device is used for feeding tube insertion or intubation insertion verification. The adapter includes an air chamber and an integrally attached display portion outside said air chamber for displaying information. The display portion and adapter may be constructed by molding into an integral portion and made out of biocompatible plastic material. The method comprises releasably attaching an electronic monitoring device portion to said airway adapter, such that a top surface of said monitoring device portion rests beneath a bottom surface of said display portion. The method further comprises determining proper tube insertion by measuring the respiratory gas of said patient through the monitoring device, wherein said monitoring device measures respiratory gas by emitting infrared light through said air chamber, sensing light energy absorption, and providing results of said energy absorption to said display portion; and releasing said monitoring device portion from said airway adapter. The adapter may then be disposed of since it is for single patient use. The electronic monitoring device is powered by a power source such as a battery, the device comprises electronic components and circuitry connected to the power source and further connected to an infrared light emitting means and sensing means. The circuit board is further connected to an indicator such as one or more light emitting diodes and/or sound emitters for indicating the results of the respiratory gas measurement.

Throughout the description and drawings, example embodiments are given with reference to specific configurations. It will be appreciated by those of ordinary skill in the art that the present invention can be embodied in other specific forms. Those of ordinary skill in the art would be ale to practice such other embodiments without undue experimentation. The scope of the present invention, for the purpose of the present patent document, is not limited merely to the specific example embodiments of the foregoing description.

I claim:
1. A device for respiratory gas monitoring comprising:
a disposable airway adapter including one or more airway connections, at least one connection having an end leading to a patient's body and another end meeting at an airway chamber sealed from outside air, the chamber providing for infrared light to pass through;
a monitoring device portion having a top surface and a recessed section, the monitoring device being releasably attachable to the airway adapter around the airway chamber at the recessed section;
a display portion integrally connected to said airway adapter, having a top surface and a bottom surface, the bottom surface partly resting upon the top surface of the monitoring device during attachment;
wherein the monitoring device portion comprises components for emitting infrared light and taking measurements of infrared light energy absorption, and the display portion displays one or more results of said measurements;
wherein the monitoring device portion comprises a circuit board and electronic circuitry connected to an infrared sensor and a battery, the circuit board further connected to one or more light emitting diodes (LEDs); and
wherein the display portion further comprises a display screen sealed within the display portion, the bottom surface of the display portion comprises a clear surface for allowing light from said LEDs to emit through and hit the display screen.

2. The device according to claim 1, wherein the chamber of the adapter comprises a plurality of depressions on an outside surface of the chamber, and the recessed portion comprises a plurality of corresponding detents for latching with said depressions when attaching the adapter to the monitoring device portion.

3. The device according to claim 1, wherein the chamber comprises opposing windows through which infrared light passes from the monitoring device portion.

4. The device according to claim 1, wherein the results of said measurements is displayed from the top surface of the display portion.

5. The device according to claim 1, wherein parts of the display screen are concealed to prevent light from emitting through, leaving unconcealed parts to allow light to pass through and be displayed.

6. A device for respiratory gas monitoring comprising:
a disposable airway adapter including one or more airway connections, at least one connection having an end leading to a patient's body and another end meeting at an airway chamber sealed from outside air, the chamber providing for infrared light to pass through;
a monitoring device portion having a top surface and a recessed section, the monitoring device being releasably attachable to the airway adapter around the airway chamber at the recessed section;
a display portion integrally connected to said airway adapter, having a top surface and a bottom surface, the bottom surface partly resting upon the top surface of the monitoring device during attachment; wherein the monitoring device portion comprises components for emitting infrared light and taking measurements of infrared light energy absorption, and the display portion displays one or more results of said measurements;
wherein the monitoring device portion comprises a circuit board and electronic circuitry connected to an infrared sensor and a battery, the circuit board further connected to one or more light emitting diodes (LEDs); and
wherein the display portion further comprises a display screen on the top surface of the display portion, the bottom surface of the display portion comprises a clear surface for allowing light from said LEDs to emit through and hit the display screen.

7. The device according to claim 6, wherein parts of the display screen are concealed to prevent light from emitting through, leaving unconcealed parts to allow light to pass through and be displayed.

8. A device for intubation verification and respiratory gas monitoring:
- a disposable airway adapter including a first airway connection having an end leading to an endotracheal tube and another end meeting at an airway chamber sealed from outside air, and a second airway connection having an end leading to a resuscitator bag and another end meeting at the chamber, wherein the chamber provides for infrared light to pass through;
- a monitoring device portion having a top surface and a recessed section, the monitoring device being releasably attachable to the airway adapter around the airway chamber at the recessed section; a display portion integrally connected to said airway adapter, having a top surface and a bottom surface, the bottom surface partly resting upon the top surface of the monitoring device during attachment;
- wherein the monitoring device portion comprises components for emitting infrared light and taking measurements of infrared light energy absorption, and the display portion displays one or more results of said measurements;
- wherein the monitoring device portion comprises a circuit board and electronic circuitry connected to an infrared sensor and a battery, the circuit board further connected to one or more light emitting diodes (LEDs); and
- wherein the display portion further comprises a display screen sealed within the display portion, the bottom surface of the display portion comprises a clear surface for allowing light from said LEDs to emit through and hit the display screen.

9. The device according to claim 8, wherein the chamber of the adapter comprises a plurality of depressions on an outside surface of the chamber, and the recessed portion comprises a plurality of corresponding detents for latching with said depressions when attaching the adapter to the monitoring device portion.

10. The device according to claim 8, wherein the chamber comprises opposing windows through which infrared light passes from the monitoring device portion.

11. The device according to claim 8, wherein the results of said measurements is displayed from the top surface of the display portion.

12. The device according to claim 8, wherein the adapter and display portion are integrally molded from a transparent plastic material.

13. A device for intubation verification and respiratory gas monitoring:
- a disposable airway adapter including a first airway connection having an end leading to an endotracheal tube and another end meeting at an airway chamber sealed from outside air, and a second airway connection having an end leading to a resuscitator bag and another end meeting at the chamber, wherein the chamber provides for infrared light to pass through;
- a monitoring device portion having a top surface and a recessed section, the monitoring device being releasably attachable to the airway adapter around the airway chamber at the recessed section;
- a display portion integrally connected to said airway adapter, having a top surface and a bottom surface, the bottom surface partly resting upon the top surface of the monitoring device during attachment;
- wherein the monitoring device portion comprises components for emitting infrared light and taking measurements of infrared light energy absorption, and the display portion displays one or more results of said measurements; and wherein the monitoring device portion comprises a circuit board and electronic circuitry connected to an infrared sensor and a battery, the circuit board further connected to one or more light emitting diodes (LEDs); and
- wherein the display portion further comprises a display screen, the bottom surface of the display portion comprises a clear surface for allowing light from said LEDs to emit through and hit the display screen.

14. The device according to claim 13, wherein the display screen is attached on the top surface of the display portion.

15. The device according to claim 13, wherein parts of the display screen are concealed to prevent light from emitting through, leaving unconcealed parts to allow light to pass through and be displayed.

16. A method for respiratory gas monitoring and tube insertion verification comprising: connecting a disposable airway adapter to a tube configured to be placed in a patient's body, the adapter having an air chamber and an integrally attached display portion outside said air chamber for displaying information;
- wherein the display portion further comprises a display screen sealed within the display portion;
- wherein the monitoring portion comprises a circuit board and electronic circuitry connected to an infrared sensor and a battery, the circuit board further connected to one or more light emitting diodes (LEDs);
- releasably attaching an electronic monitoring device portion to said airway adapter, such that a top surface of said monitoring device portion rests beneath a bottom surface of said display portion and allows light from said LEDs to emit through and hit the display screen;
- determining proper tube insertion by measuring the respiratory gas of said patient through the monitoring device, wherein said monitoring device measures respiratory gas by emitting infrared light through said air chamber, sensing light energy absorption, and providing results of said energy absorption to said display portion; and
- releasing said monitoring device portion from said airway adapter.

17. The method according to claim 16 wherein the adapter and display portion are integrally molded from a transparent plastic material.

* * * * *